United States Patent
Hamada et al.

(10) Patent No.: US 9,131,935 B2
(45) Date of Patent: Sep. 15, 2015

(54) RETRACTOR

(75) Inventors: James S. Hamada, Torrance, CA (US);
Scott Jones, McMurray, PA (US);
Brandon Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 823 days.

(21) Appl. No.: 13/251,608

(22) Filed: Oct. 3, 2011

(65) Prior Publication Data

US 2012/0083662 A1    Apr. 5, 2012

Related U.S. Application Data

(60) Provisional application No. 61/388,702, filed on Oct. 1, 2010.

(51) Int. Cl.
*A61B 1/32* (2006.01)
*A61B 17/02* (2006.01)

(52) U.S. Cl.
CPC ......... *A61B 17/0293* (2013.01); *A61B 17/0206* (2013.01)

(58) Field of Classification Search
CPC ............... A61B 17/02; A61B 17/0218; A61B 17/0293; A61B 17/0206
USPC ................. 600/201, 204, 208, 213–215, 219, 600/221–222, 225–231, 233, 235, 210
See application file for complete search history.

(56) References Cited

U.S. PATENT DOCUMENTS

| | | | |
|---|---|---|---|
| 563,236 A | 6/1896 | Penhall | |
| 4,263,899 A | 4/1981 | Burgin | |
| 4,616,635 A * | 10/1986 | Caspar et al. | 600/215 |
| 4,747,394 A | 5/1988 | Watanabe | |
| 5,125,396 A | 6/1992 | Ray | |
| 5,509,893 A | 4/1996 | Pracas | |
| 5,681,265 A | 10/1997 | Maeda et al. | |
| 5,785,648 A | 7/1998 | Min | |
| 5,928,139 A | 7/1999 | Koros et al. | |
| 5,944,658 A | 8/1999 | Koros et al. | |
| 6,042,540 A | 3/2000 | Johnston et al. | |
| 6,083,154 A | 7/2000 | Liu et al. | |
| 6,096,046 A | 8/2000 | Weiss | |
| 6,139,493 A | 10/2000 | Koros et al. | |
| 6,159,231 A * | 12/2000 | Looney et al. | 606/206 |
| 6,200,322 B1 | 3/2001 | Branch et al. | |
| 6,224,545 B1 | 5/2001 | Cocchia et al. | |
| 6,283,912 B1 | 9/2001 | Hu et al. | |
| 6,361,492 B1 | 3/2002 | Santilli | |
| 6,371,911 B1 | 4/2002 | Hossain et al. | |

(Continued)

*Primary Examiner* — Anu Ramana
*Assistant Examiner* — Jessica Weiss
(74) *Attorney, Agent, or Firm* — Carter, DeLuca, Farrell & Schmidt, LLP

(57) ABSTRACT

A retractor for use in spinal procedures is disclosed. The retractor includes a first frame member defining a first recess and a second frame member pivotally connected to the first frame member. The second frame member defines a second recess. The retractor further includes a first blade assembly operably received within the first recess and a second blade assembly operably received within the second recess. The first blade assembly includes a first blade configured to pivot relative to the first frame member and a first blade extender selectively extendable from the first blade. The second blade assembly includes a second blade configured to translate within the second recess and a second blade extender selectively extendable from the second blade.

22 Claims, 10 Drawing Sheets

(56) References Cited

U.S. PATENT DOCUMENTS

| | | |
|---|---|---|
| 6,450,952 B1 | 9/2002 | Rioux et al. |
| 6,616,605 B2 | 9/2003 | Wright et al. |
| 6,896,654 B2 | 5/2005 | Paolitto et al. |
| 6,945,933 B2 | 9/2005 | Branch et al. |
| 7,758,501 B2 * | 7/2010 | Frasier et al. ............ 600/233 |
| 2007/0038216 A1 * | 2/2007 | Hamada ............ 606/53 |
| 2007/0156026 A1 * | 7/2007 | Frasier et al. ............ 600/224 |
| 2008/0188718 A1 * | 8/2008 | Spitler et al. ............ 600/213 |
| 2011/0130793 A1 * | 6/2011 | Woolley et al. ............ 606/279 |

\* cited by examiner

RETRACTOR

CROSS-REFERENCE TO RELATED APPLICATION

This application claims the benefit of and priority to Provisional Application Ser. No. 61/388,702 filed on Oct. 1, 2010, the content of which is incorporated by reference herein in its entirety.

BACKGROUND

1. Technical Field

The present disclosure relates to orthopedic surgery. More particularly, the present disclosure relates to retractors for use in orthopedic surgery.

2. Background Art

The human spinal column is a highly complex structure. It includes twenty-four (24) discrete bones, known as vertebrae, coupled sequentially to one another to house and protect critical elements of the nervous system. The spine is a flexible structure capable of a large range of motion. There are various disorders, diseases and types of injury which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

Spinal fixation apparatuses are widely employed in surgical processes for correcting spinal injuries and diseases. Recently, there has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and may be modified to fit the contours of these small incisions, however, these hand-held retractors require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a thirty to forty millimeter (30-40 mm) rod to be introduced into a one centimeter (1 cm) incision and a multilevel fusion may require a rod several inches long to fit into the same sized incision.

For this reason, it is important that the minimal incision be maintained in an open and accessible condition (i.e. as wide as practicable) for introduction of the rod. Minimally invasive surgery offers significant advantages over conventional open surgery. For example, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

In order to be truly minimally invasive, a spine fusion procedure should have a minimum number of small incisions and not require significant tissue and/or muscle retraction. A muscle sparing approach is preferred where the muscle is bluntly dissected with a finger or other blunt instrument. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

A retractor for performing a microdiscectomy or a one level fusion while a patient is positioned in a posterior (lying face down) or lateral (side lying) position is provided. The retractor includes a first frame member defining a first recess and a second frame member pivotally connected to the first frame member. The second frame member defines a second recess. The retractor further includes a first blade assembly operably received within the first recess and a second blade assembly operably received within the second recess. The first blade assembly includes a first blade configured to pivot relative to the first frame member and the second blade assembly includes a second blade configured to translate within the second recess.

The first and second frame members of the retractor are substantially C-shaped. The first blade assembly may include a first blade extension extending from the first blade and the second blade assembly may include a second blade extension extending from the second blade. Each of the first and second blade extensions may include a cut-out. The first blade assembly may include a first screw for selectively moving the first blade extension relative to the first blade and the second blade assembly may include a second screw for selectively moving the second blade relative to the second blade.

In one embodiment, the first frame member includes an adjustment mechanism for pivoting the first blade assembly relative to the first frame member. The second frame assembly may include a translation assembly for selectively translating the second blade assembly relative to the second frame member. The first frame member may define a pair of slots configured for operable engagement with a first instrument for securing the first frame member as the second frame member is pivoted relative to the first frame member. The second frame member may define a pair of slots configured for operable engagement with a second instrument for facilitating the pivoting of the second frame member relative to the first frame member.

The second frame member may include a locking mechanism for selectively locking the second blade assembly relative to the second frame member. The first frame member may also include a locking mechanism for locking the first frame member relative to the second frame member.

BRIEF DESCRIPTION OF THE DRAWINGS

Embodiments of a retractor according to the present disclosure are disclosed herein with reference to the drawings, wherein.

DETAILED DESCRIPTION

Figure 1:
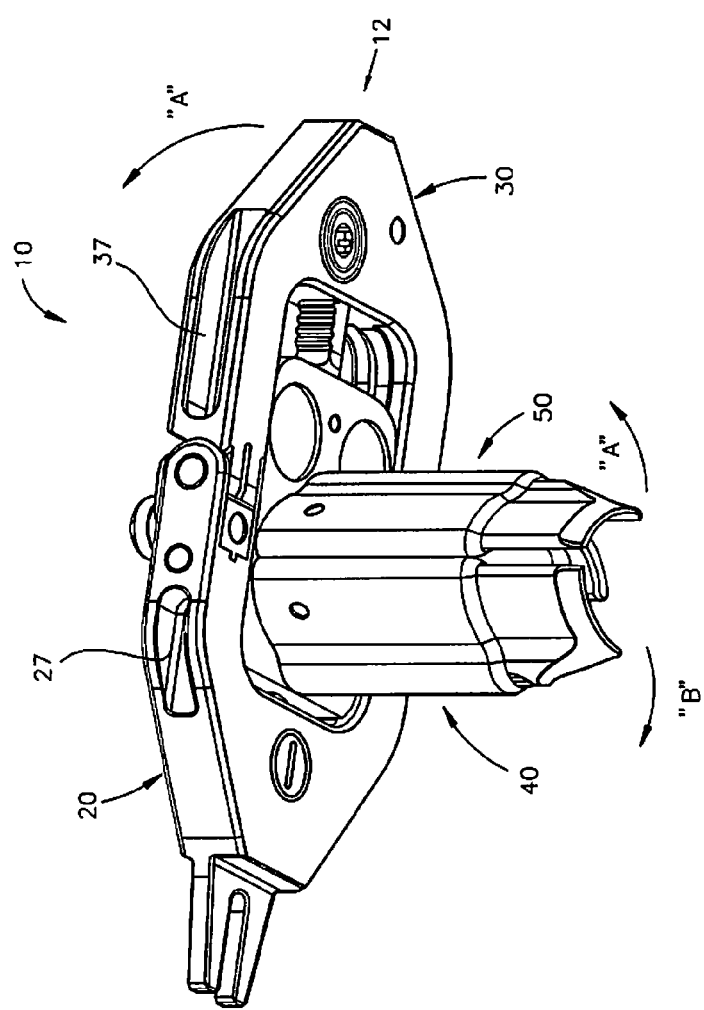
FIG. 1 is a perspective view of a retractor according to the present disclosure, wherein the first and second blade assemblies are in a first or closed position.

With reference to the FIGS. 1-6, an embodiment of a retractor according to an embodiment of the present disclosure is shown generally as retractor 10. Although, as will be discussed in further detail below, retractor 10 may be configured for use in a microdiscectomy and/or a one level fusion while a patient is positioned in a posterior (lying face down) or lateral (side lying) position, it is envisioned that retractor 10 may be used in myriad of procedures and while a patient is in various positions. With particular reference to FIG. 1, retractor 10 includes a frame 12 and first and second blade assemblies 40, 50 operably connected to frame 12.

Figure 2:
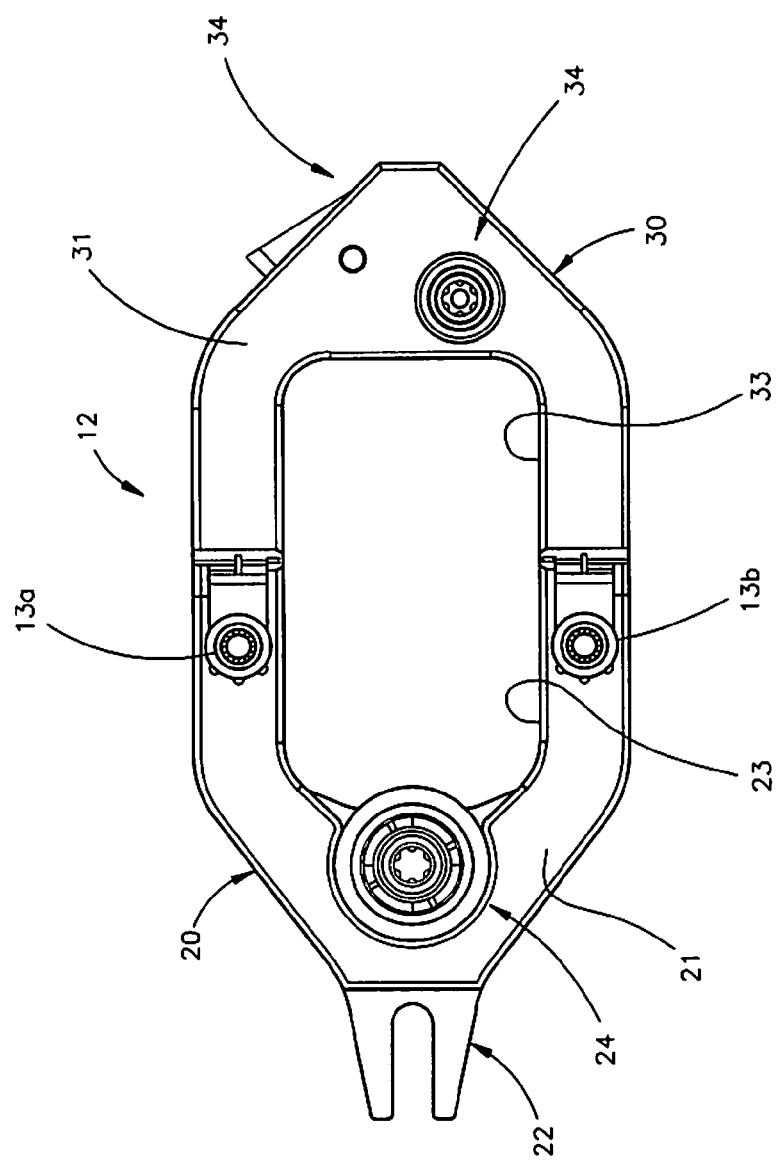
FIG. 2 is a top view of the frame of the retractor of FIG. 1, with the first and second blade assemblies removed.

With reference to FIG. 2, frame 12 includes a static portion 20 and a dynamic portion 30. Dynamic portion 30 is connected to static portion 20 such that dynamic portion 30 may be pivoted relative to static portion 20, as indicated by arrows "A" (FIG. 1). Each of static and dynamic portions 20, 30 includes a substantially C-shaped member 21, 31, respectively, defining a recess 23, 33, respectively. Recess 23 is configured to operably receive first blade assembly 40 therein and recess 33 is configured to operably receive second blade assembly 50 therein.

Referring back to FIG. 1, dynamic portion 30 of frame 12 defines a pair of slots 37 (FIG. 1) formed along an outer edge thereof configured to receive a pair of members of a first instrument "$I_1$" (FIG. 12) for assisting in pivoting dynamic portion 30 relative to static portion 20. Static portion 20 defines a corresponding pair of slots 27 configured to receive a pair of members of a second instrument "$I_2$" (FIG. 12) for assisting in stabilizing static portion 20 while dynamic portion 30 is pivoted relative thereto. In an alternative embodiment, each of static portion 20 and dynamic portion 30 may include a protrusion (not shown) formed on outer edges thereof for engagement by first and second instruments (not shown).

A pair of locking members 13a, 13b selectively lock dynamic portion 30 relative to static portion 20. As shown, locking members 13a, 13b include locking screws, however, it is envisioned that locking members 13a, 13b may include any suitable locking mechanism, including, for example, sliding locks.

With reference still to FIG. 1, static portion 20 of frame 12 includes a mounting feature 22. As shown, mounting feature 22 includes a fork member extending from static portion 20 and configured for optional selective engagement by a standard table mount arm "M" (FIG. 11) for securing retractor 10 relative to an operating platform (not shown).

With reference to FIG. 2, static portion 20 of frame 12 includes an adjustment mechanism 24. Adjustment mechanism 24 pivots blade assembly 40 relative to static portion 20. In one embodiment, adjustment mechanism 24 is disposed within static portion 20 of frame 12. In this manner, no portion of adjustment mechanism 24 interferes with the manipulation of one or more instruments (not shown) that have been inserted through opening 5 defined between blade assemblies 40, 50.

Dynamic portion 30 includes a translation mechanism 34. Translation mechanism 34 laterally translates second blade assembly 50 within recess 33 of dynamic portion 30. In one embodiment, translation mechanism 34 is disposed within static portion 20 of frame 12. In this manner, no portion of translation mechanism 34 interferes with the manipulation of any instrument (not shown) that has been inserted through opening 5 defined between blade assemblies 40, 50.

With reference now to FIGS. 3-6, first blade assembly 40 (FIGS. 3 and 4) and second blade assembly 50 (FIGS. 5 and 6) each include a blade 42, 52, respectively, and a blade extender 44, 54, respectively, extending from a distal end 42b, 52b of respective blades 42, 52. As shown, each of first and second blades 42, 52 and first and second blade extenders 44, 54 of respective first and second blade assemblies 40, 50 are substantially curved. When placed adjacent to one another blade assemblies 40, 50 define an opening 5 therebetween.

First and second blades 42, 52 and first and/or second blade extenders 44, 54 of respective first and second blade assemblies 40, 50 may be formed from any bio compatible material, including but not limited to polyetheretherketone (PEEK), polysulfone (RADEL), polyetherimide (ULTEM), stainless steel, titanium (both allow and commercially pure), cobalt chrome, and aluminum.

With reference still to FIGS. 3-6, as shown, each of blade assemblies 40, 50 includes a screw 45, 55 extending into respective blade extenders 44, 54 for extending and retracting blade extenders 44, 54 relative to respective blades 42, 52. Screws 45, 55 are locked to respective blades 42, 52 by a spring clip 47, 57, respectively. Alternatively, screws 45, 55 may be locked to blades 42, 52 with laser welding, O-rings or tacking. Blade assemblies 40, 50 are configured such that blade extenders 44, 54 may be extended prior to or after insertion of first and second blades 42, 52 through an incision. Each of first and second blade extenders 44, 54 includes a cut-out portion 43, 53 to accommodate the anatomy of a patient.

Figure 4:
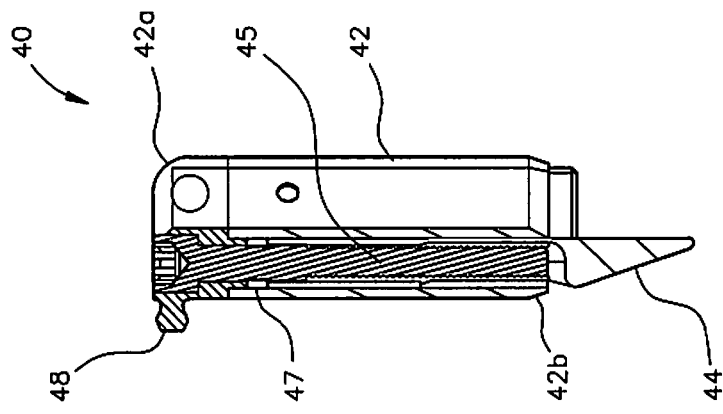
FIG. 4 is a side view of the first blade assembly of FIG. 3.
Figure 3:
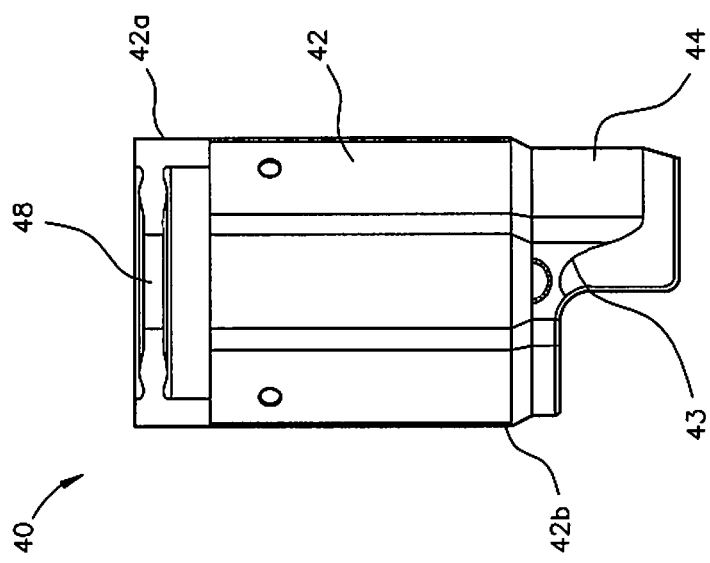
FIG. 3 is a front view of the first blade assembly of the retractor of FIGS. 1 and 2.

With particular reference to FIGS. 3 and 4, first blade assembly 40 further includes a flange 48 formed on a proximal end 42a of blade 42. Flange 48 is configured to engage adjustment mechanism 24 (FIG. 2) within static portion 20 of frame 12.

Figure 6:
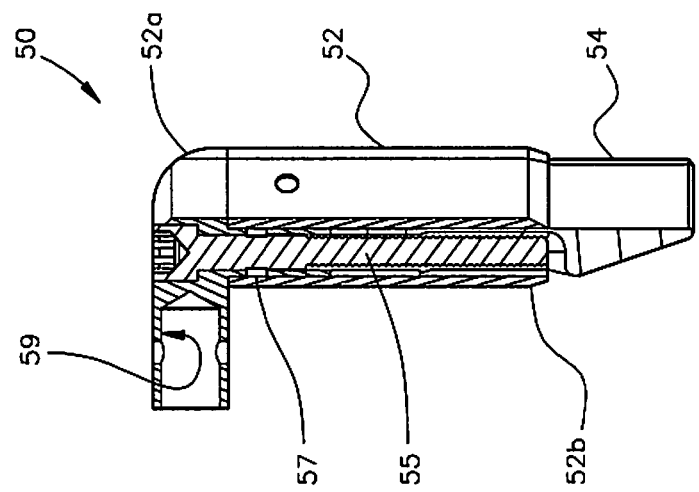
FIG. 6 is a side view of the second blade assembly of FIG. 5.
Figure 5:
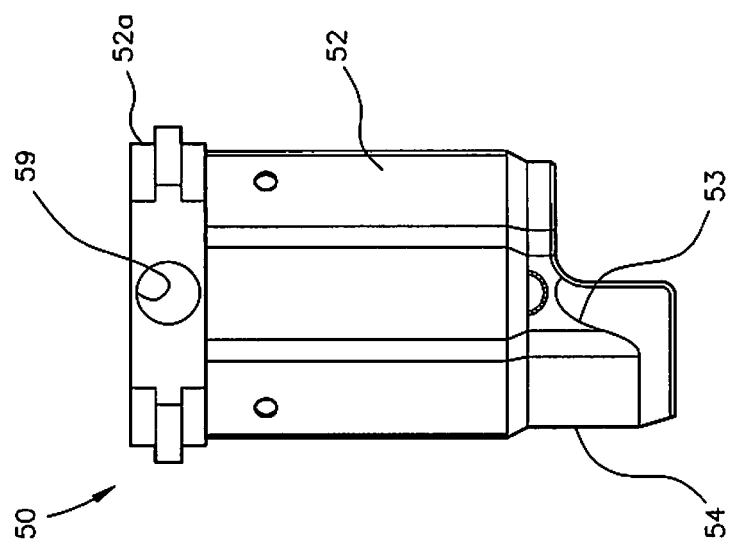
FIG. 5 is a front view of the second blade assembly of the retractor of FIGS. 1 and 2.
Figure 7:
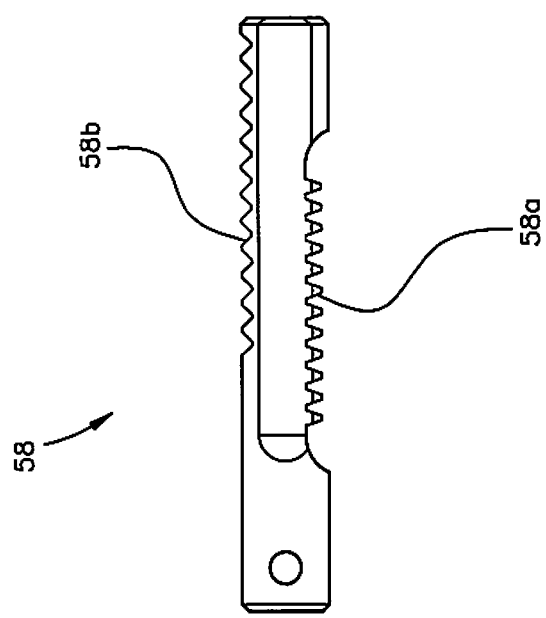
FIG. 7 is a top view of a rack member of the retractor of FIGS. 1 and 2.

Turning now to FIGS. 5 and 6, second blade assembly 50 further includes a recess 59 formed in proximal end 52a of blade 52. Recess 59 is configured to receive a rack member 58 (FIG. 7) therein. Rack member 58 is configured to engage translation mechanism 34 within dynamic portion 30 of frame 12. Rack member 58 is configured to extend from blade assembly 50 and includes a first set of teeth 58a configured to selectively engage a pinion 36 of translation mechanism 34 mounted with dynamic portion 30 of frame 12. Rack member 58 further includes a second set of teeth 58b for selective engagement with a release button 38 of translation mechanism 34.

Figure 8:
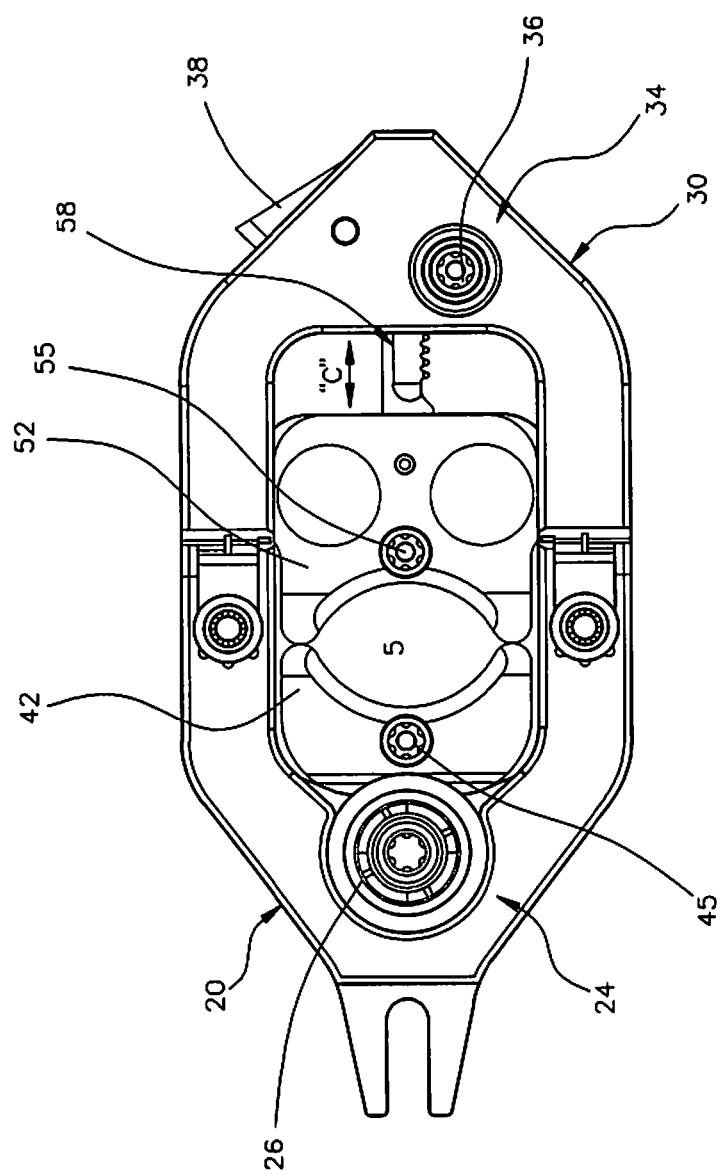
FIG. 8 is a top view of the retractor of FIGS. 1 and 2.
Figure 9:
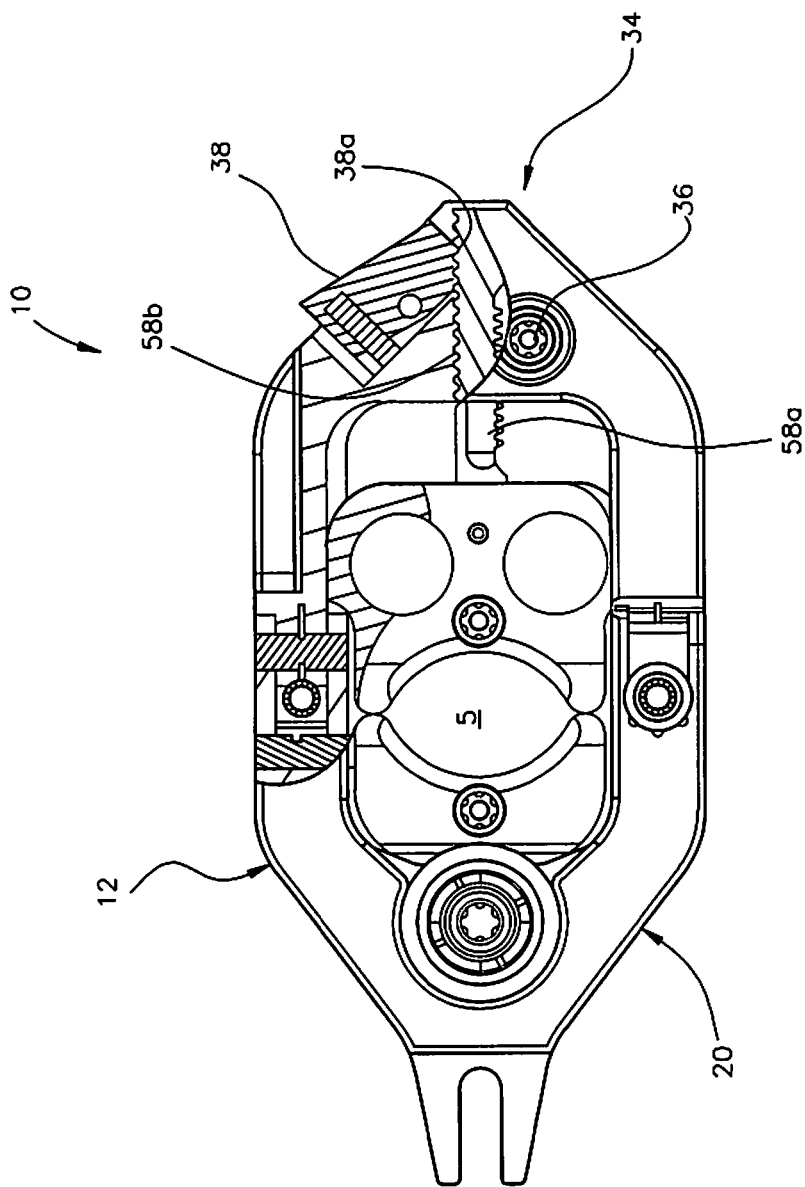
FIG. 9 a partial cut-away top view of the retractor of FIG. 8.

Referring now to FIGS. 8 and 9, as discussed above, second blade assembly 50 is adjustably received within recess 33 of dynamic portion 30 of frame 12 and is configured to be laterally translated therein. Rack member 58 is securely affixed to and extends from blade assembly 50. Rotation of pinion 36 of adjustment mechanism 34 causes lateral translation of rack member 58, and thus, second blade assembly 50 within recess 33 of dynamic portion 30, as indicated by arrows "C". As noted above, adjustment mechanism 34 further includes release button 38. Release button 38 includes a set of teeth 38a (FIG. 9) configured to selectively engage second set of teeth 58b of rack assembly 58. Depression of release button 38 causes teeth 38a to disengage second set of teeth 58b of rack member 58 and permit lateral translation of second blade assembly 50. Release of release button 38 causes teeth 38a to reengage rack member 58, thereby locking second blade assembly 50 relative to dynamic portion 30 of frame 12.

Figure 10:
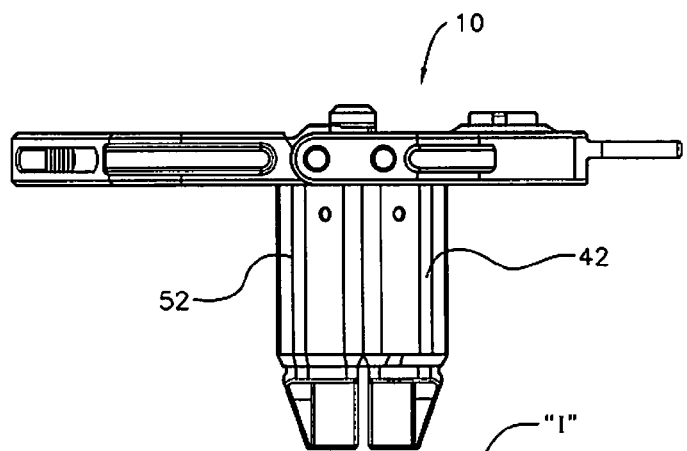
FIG. 10 is a side view of the retractor of FIGS. 1 and 2 prior to insertion through an incision.
Figure 11:
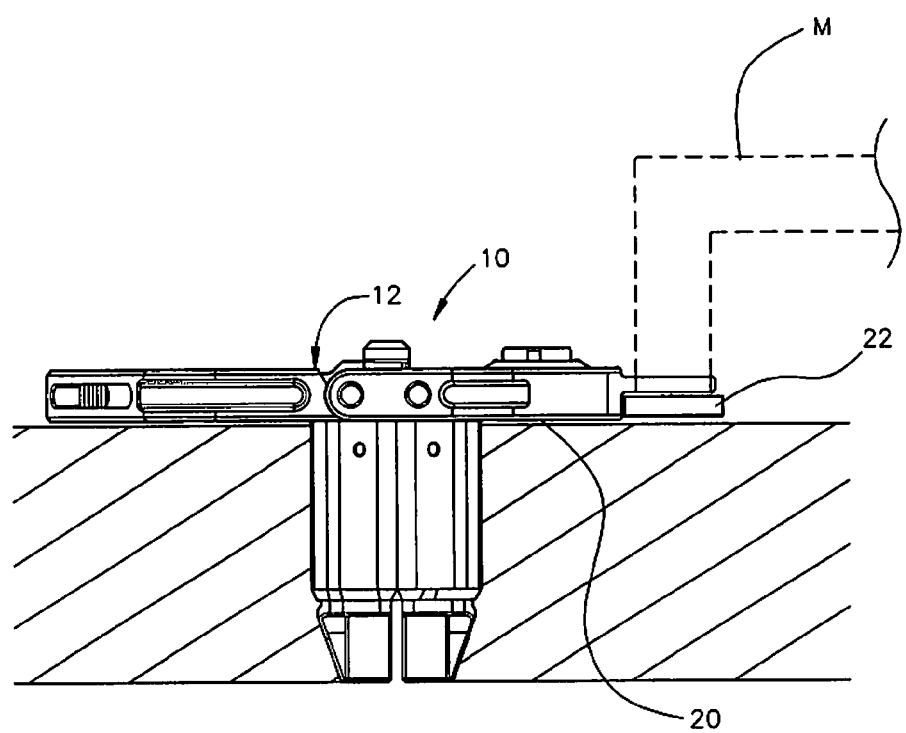
FIG. 11 is a side view of the retractor of FIG. 10 after being inserted through the incision and operably connected to a mount arm.

With reference now to FIGS. 10-14, the use of retractor 10 will be described. With reference initially to FIG. 10, during a procedure using retractor 10, an incision "I" is first made through the tissue "T" in a patient and a standard blunt instrument (not shown), such as an obturator, dilator, or finger, is used to bluntly dissect down through the tissue "T", i.e., skin and muscle, to the disc space. With blade assemblies 40, 50 in a closed position, as seen in FIG. 10, blades 42, 52 and blade extenders 44, 54 of retractor 10 are received through the incision. Turning to FIG. 11, retractor 10 optionally may then be anchored to the surgical table by attaching a standard surgical arm member "M" to mounting feature 22 on static portion 20 of frame 12.

Figure 12:
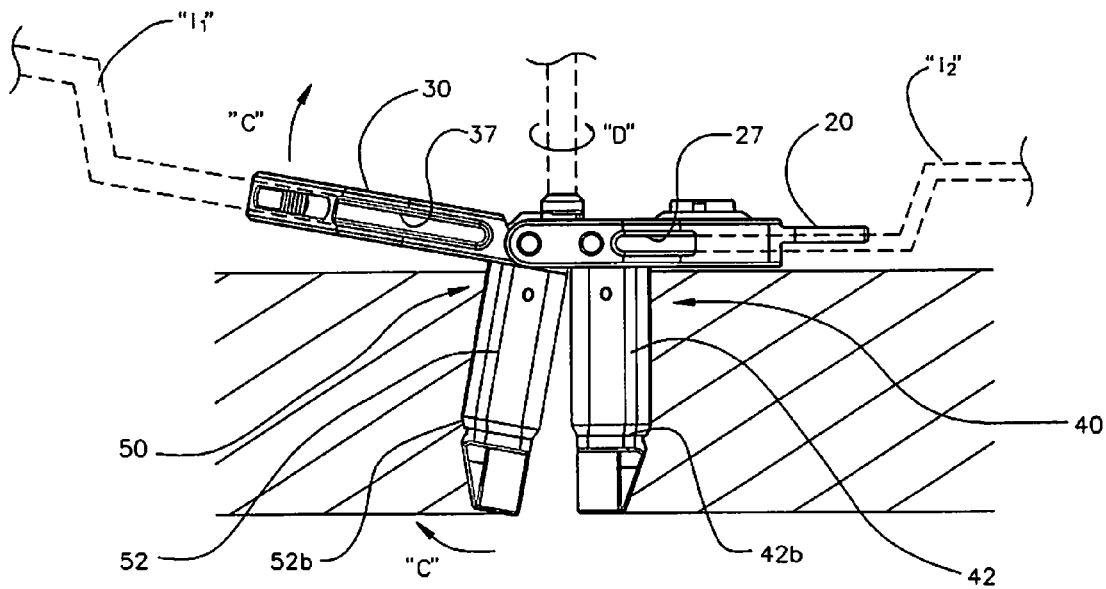
FIG. 12 is a side view of the retractor of FIGS. 10 and 11 with a second frame member pivoted relative to a first frame member.

Referring now to FIG. 12, once first and second blades 42, 52 of respective blade assemblies 40, 50 are received through the incision, dynamic portion 30 of frame 12 may be pivoted relative to static portion 20 of frame 12, as indicated by arrow "C", to cause distal end 52b of second blade 52 of second blade assembly 50 to move away from distal end 42b of first blade 42 of first blade assembly 40, as indicated by arrow "C". As discussed above, a portion of first instrument "I$_1$" (shown in phantom) received within slots 37 formed along an outer edge of dynamic portion 30 may be used to facilitate pivoting of dynamic portion 30 while a portion of second instrument "I$_2$" (shown in phantom) is received within slots 27 formed along an outer edge of static portion 20 to facilitate maintaining static portion 20 an a locked position. Once pivoted as necessary, locking screws 13a, 13b are tightened to lock dynamic portion 30 relative to static portion 20, as indicated by arrow "D". Screws 13a, 13b may be tightened by hand, or alternatively, as shown, by a screw drive or other driving device.

Figure 13:
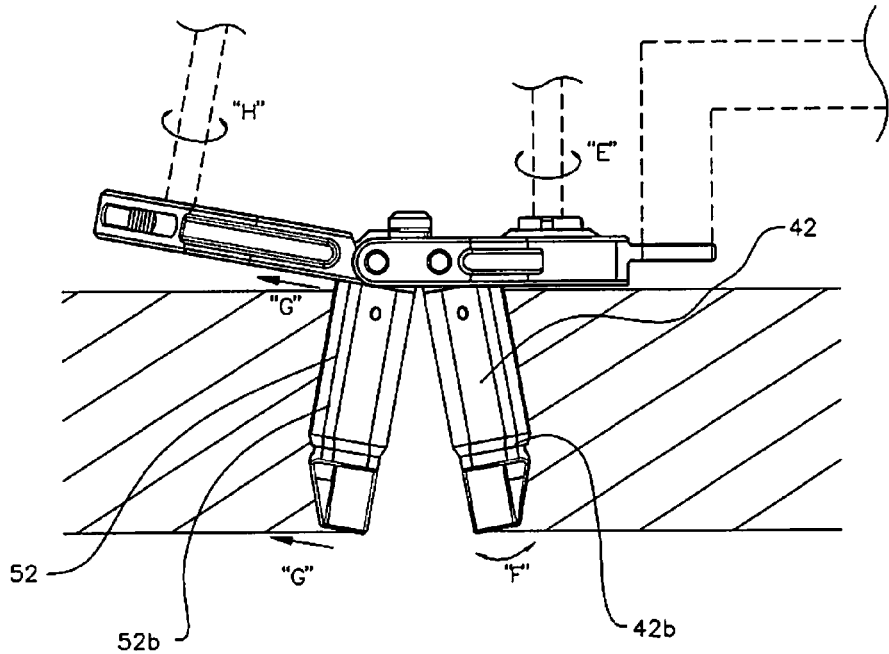
FIG. 13 is a side view of the retractor of FIGS. 10-12, with the first blade member pivoted relative to the first frame member.

With reference to FIG. 13, distal end 42b of first blade 42 may be pivoted away from distal end 52b of second blade 52. As discussed above, static portion 20 of frame 12 includes adjustment mechanism 24. Adjustment mechanism 24 includes an adjustment screw 26 which is configured to pivot blade 42 of blade assembly 40 relative to static portion 20. Rotation of adjustment screw 26, as indicated by arrow "E", causes distal end 42b of blade 42 to pivot towards or away from distal end 52b of second blade 52, as indicated by arrow "F". Blade 52 of second blade assembly 50 may also be moved laterally with respect to first blade 42 of first blade assembly 40, as indicated by arrow "G". Rotation of pinion 36 of translation mechanism 34, as indicated by arrow "H", causes second blade 52 of second blade assembly 50 to translate relative to first blade 42 of first blade assembly 40.

Figure 14:
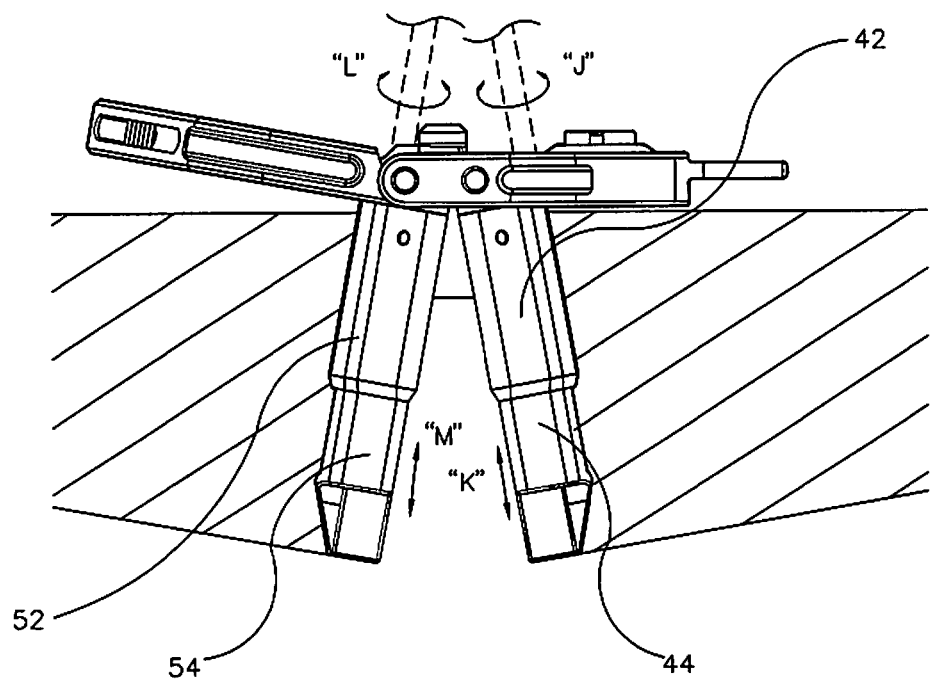
FIG. 14 is a side view of the retractor of FIGS. 10-13, with each of the first and second blade extenders of the first and second blade assemblies extended relative to respective first and second blades.

With reference to FIG. 14, prior to or subsequent to insertion of first and second blades 42, 52 of first and second blade assemblies 40, 50, respectively, through incision "I", either or both of first and second blade extenders 44, 54 may be extended relative to respective first and second blades 42, 52. Rotation of set screw 45 (FIG. 8), as indicated by arrow "J", causes the extension/retraction of first blade extender 44 relative to first blade 42, as indicated by arrow "K". Rotation of set screw 55 (FIG. 8), as indicated by arrow "L", causes the extension/retraction of second blade extender 54 relative to second blade 52, as indicated by arrow "M".

Removal of retractor 10 from with the incision is performed in reverse order of insertion.

It will be understood that various modifications may be made to the embodiments disclosed herein. By way of example only, it is contemplated that both retractor blades may be mounted to pivot relative to their respective frame portions. Therefore, the above description should not be construed as limiting, but merely as exemplifications of particular embodiments. Those skilled in the art will envision other modifications within the scope and spirit of the claims appended hereto.

What is claimed is:

1. A retractor comprising:
a first frame member defining a first recess;
a second frame member pivotally connected to the first frame member, the second frame member defining a second recess; a locking member extending through a top surface and a bottom surface of the second frame member for securing the first and second frame members in a fixed position relative to each other;
a first blade assembly operably received within the first recess, the first blade assembly including a first blade configured to pivot relative to the first frame member, a first blade extender selectively extendable from the first blade, and a first screw for selectively moving the first blade extender relative to the first blade; and a second blade assembly operably received within the second recess, the second blade assembly including a second blade configured to translate within the second recess, a second blade extender selectively extendable from the second blade, and a second screw for selectively moving the second blade extender relative to the second blade.

2. The retractor of claim 1, wherein the first and second frame members are substantially C-shaped.

3. The retractor of claim 1, wherein each of the first and second blade extenders includes a cut-out.

4. The retractor of claim 1, wherein the first frame member includes an adjustment mechanism for pivoting the first blade assembly relative to the first frame member.

5. The retractor of claim 4, wherein the adjustment mechanism is disposed within the first frame member.

6. The retractor of claim 1, wherein the second frame member includes a translation assembly for selectively translating the second blade assembly relative to the second frame member.

7. The retractor of claim 6, wherein the translation assembly is disposed within the second frame member.

8. The retractor of claim 1, wherein the first frame member defines a pair of slots configured for operable engagement with a first instrument for securing the first frame member as the second frame member is pivoted relative to the first frame member.

9. The retractor of claim 8, wherein the second frame member defines a pair of slots configured for operable engagement with a second instrument for facilitating the pivoting of the second frame member relative to the first frame member.

10. The retractor of claim 1, wherein rotation of the first screw in a first direction extends the first blade extender relative to the first blade, and rotation of the second screw in the first direction extends the second blade extender relative to the second blade.

11. The retractor of claim 10, wherein rotation of the first screw in a second direction retracts the first blade extender relative to the first blade, and rotation of the second screw in the second direction retracts the second blade extender relative to the second blade.

12. The retractor of claim 1, wherein the first screw includes a first threaded portion in operable engagement with the first blade extender and the second screw includes a second threaded portion in operable engagement with the second blade extender.

13. The retractor of claim 1, wherein the first blade extender is selectively retractable relative to the first blade and the second blade extender is selectively retractable relative to the second blade.

14. A method for retracting tissue, the method comprising:
providing a retractor having, a first frame member; a second frame member pivotally secured to the first frame member and including a locking member extending through a top surface and a bottom surface thereof for securing the first and second frame members in a fixed position relative to each other;
a first blade assembly operably engaged with the first frame assembly and including a first blade, a first blade extender selectively extendable from the first blade, and a first screw for selectively moving the first blade extender relative to the first blade; and
a second blade assembly operably engaged with the second frame assembly and including a second blade, a second blade extender selectively extendable from the second blade, and a second screw for selectively moving the first blade extender relative to the first blade;
receiving the first and second blades of the first and second blade assemblies through an incision; and
moving at least one of the first and second blade extenders relative to the respective first and second blades.

15. The method of claim 14, wherein the retractor further includes a first frame member defining a first recess configured to receive the first blade assembly and a second frame member pivotally connected to the first frame member, the second frame member defining a second recess configured to receive the second blade assembly.

16. The method of claim 15, further including pivoting the second frame member relative to the first frame member.

17. The method of claim 15, further including pivoting the first blade relative to the second blade.

18. The method of claim 15, further including translating the second blade relative the second frame member.

19. The method of claim 14, wherein moving at least one of the first and second blade extenders relative to the respective first and second blades includes rotating the respective first or second screw in a first direction to extend at least one of the first and second blade extenders.

20. The method of claim 19, wherein moving at least one of the first and second blade extenders relative to the respective first and second blades includes rotating the respective first or second screw in a second direction to retract at least one of the first and second blade extenders.

21. The method of claim 14, wherein the first screw includes a first threaded portion in operable engagement with the first blade extender and the second screw includes a second threaded portion in operable engagement with the second blade extender.

22. The method of claim 14, wherein moving at least one of the first and second blade extenders relative to the respective first and second blades includes extending and retracting the first and second blade extenders relative to the respective first and second blades.

* * * * *